(12) United States Patent
Shin et al.

(10) Patent No.: US 11,110,061 B2
(45) Date of Patent: Sep. 7, 2021

(54) MICROSPHERICAL SUSTAINED-RELEASE INJECTION CONTAINING ESCITALOPRAM AND METHOD FOR PREPARING SAME

(71) Applicants: KOREA RESEARCH INSTITUTE OF CHEMICAL TECHNOLOGY, Daejeon (KR); KOREA PHARMA CO., LTD., Gyeonggi-do (KR)

(72) Inventors: Byung Chul Shin, Daejeon (KR); Sun Hang Cho, Daejeon (KR); Tae Kyung Yang, Daejeo (KR); Seok Hee Kang, Seoul (KR); Eun Hee Park, Seoul (KR)

(73) Assignees: KOREA RESEARCH INSTITUTE OF CHEMICAL TECHNOLOGY; KOREA PHARMA CO., LTD.

( * ) Notice: Subject to any disclaimer, the term of this patent is extended or adjusted under 35 U.S.C. 154(b) by 0 days.

(21) Appl. No.: 16/760,995

(22) PCT Filed: Nov. 1, 2018

(86) PCT No.: PCT/KR2018/013212
§ 371 (c)(1),
(2) Date: May 1, 2020

(87) PCT Pub. No.: WO2019/088744
PCT Pub. Date: May 9, 2019

(65) Prior Publication Data
US 2020/0281856 A1 Sep. 10, 2020

(30) Foreign Application Priority Data

Nov. 1, 2017 (KR) .......................... 10-2017-0144796

(51) Int. Cl.
*A61K 9/16* (2006.01)
*A61K 31/343* (2006.01)
*A61K 9/00* (2006.01)

(52) U.S. Cl.
CPC .......... *A61K 9/1647* (2013.01); *A61K 9/1617* (2013.01); *A61K 31/343* (2013.01); *A61K 9/0019* (2013.01)

(58) Field of Classification Search
CPC .. A61K 9/1647; A61K 9/1617; A61K 31/343; A61K 9/0019
See application file for complete search history.

(56) References Cited

U.S. PATENT DOCUMENTS

| 5,718,922 A | * | 2/1998 | Herrero-Vanrell .......................... A61K 9/1647 264/4.1 |
| 8,481,064 B2 | * | 7/2013 | McKay ................ A61K 9/0024 424/422 |
| 2010/0189797 A1 | | 7/2010 | Mendlewicz |
| 2013/0217673 A1 | * | 8/2013 | Wilsey .................... A61P 25/00 514/211.04 |
| 2019/0091164 A1 | * | 3/2019 | Horhota ............... A61K 31/713 |

FOREIGN PATENT DOCUMENTS

| WO | 03002092 A2 | 1/2003 |
| WO | 03011278 A1 | 2/2003 |
| WO | 2008104880 A2 | 9/2008 |
| WO | 2012068783 A1 | 5/2012 |
| WO | 2015085004 A1 | 6/2015 |

OTHER PUBLICATIONS

International Search Report and Written Opinion, in PCT application No. KR2018/013212, dated May 10, 2019, pp. 1-4.
Yang et al., Suppression of Initial Burst in PLGA Microspheres Using Poly-meric Complex, Abstracts of the Polymer Society of Korea, 2017, p. 90, vol. 42.
Desai et al., Active self-healing encapsulation of vaccine antigens in PLGA microspheres, J Control Release, 2013, pp. 62-74, vol. 165.
Kang et al., PLGA Microsphere Addition to 1-Hydroxy-2-napthoic Acid Enhances the Sustained Release of Escitalopram, Bulletin of the Korean Chemical Society, 2019, pp. 791-795, vol. 40.

* cited by examiner

*Primary Examiner* — Robert A Wax
*Assistant Examiner* — Olga V. Tcherkasskaya
(74) *Attorney, Agent, or Firm* — Wolter VanDyke Davis, PLLC; Eugene J. Molinelli; Martha Cassidy

(57) ABSTRACT

The present invention relates to a biodegradable polymer microsphere-containing sustained-release injection containing escitalopram as an active ingredient, and to a method for manufacturing the same. In the case of escitalopram microspheres, there is a problem of low encapsulation rate, fracture due to weak strength, and initial over-release due to the phase separation of the liquid drug and the polymer inside the microspheres. In order to solve the problem, it is possible to maximize the encapsulation amount and the encapsulation efficiency of the escitalopram adding a hydrophobic solidifying agent to uniformize the non-uniform phase, to overcome the cracking of the microspheres at high loading conditions, and to properly control the initial release and release delay of the microspheres.

2 Claims, 4 Drawing Sheets

【Figure 1】
| | Full photograph of Microspheres | Enlarged Photograph of Inner Crushing Surface of Microspheres |
|---|---|---|
| (a) Example 1 | 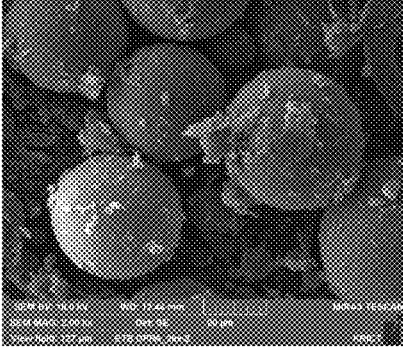 | 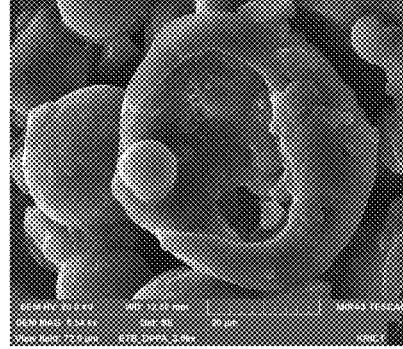 |
| (b) Example 2 | 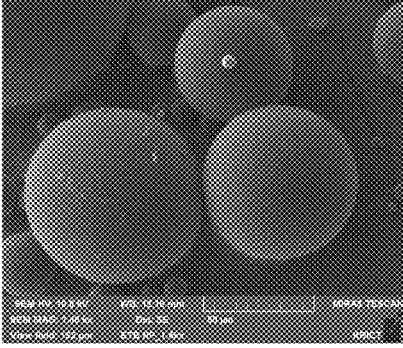 | 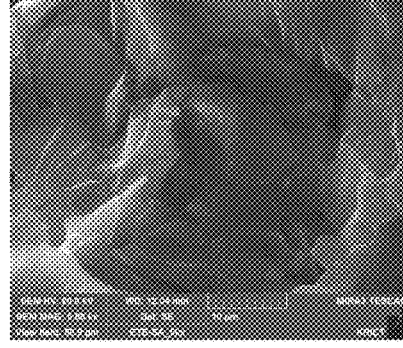 |
| (c) Example 3 | 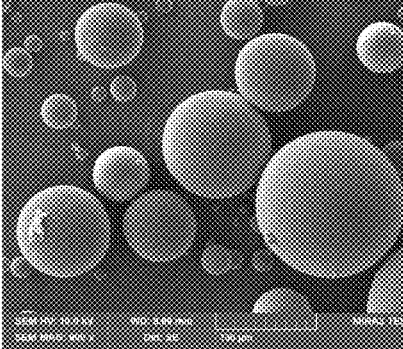 | 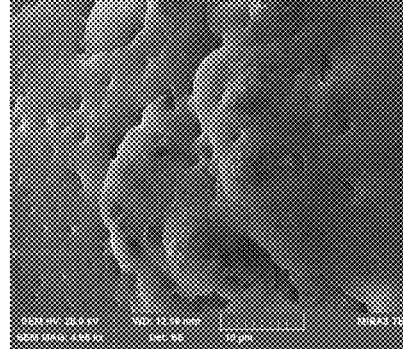 |

[Figure 2]
| (d) Comparative Example 1 | Full photo of Microspheres | Enlarged Photograph of Inner Crushed Surface of Microspheres |
|---|---|---|
| | 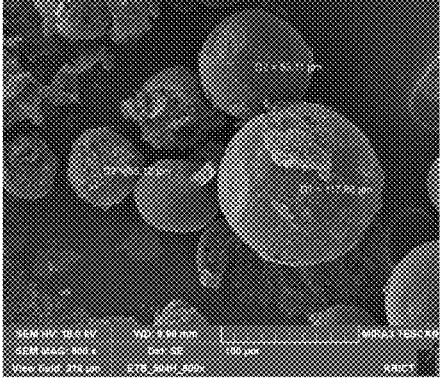 | 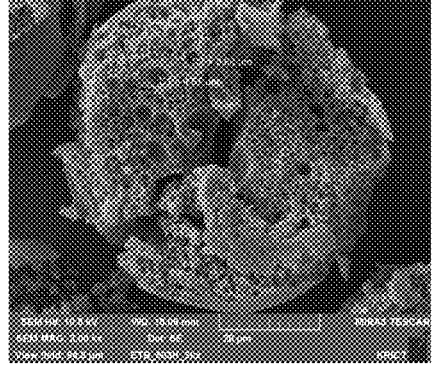 |
| | Enlarged Photograph of Inner Crushed Surface of Loading Rate 12.5% Microspheres | Enlarged Photograph of Inner Crushed Surface of Loading Rate 21% Microspheres |
| | 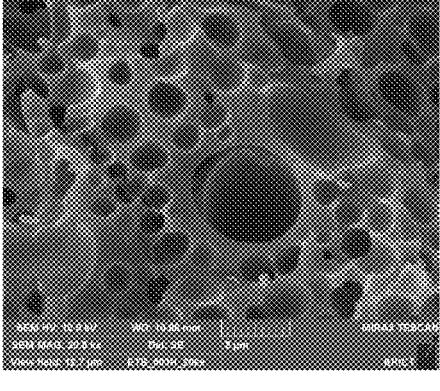 | 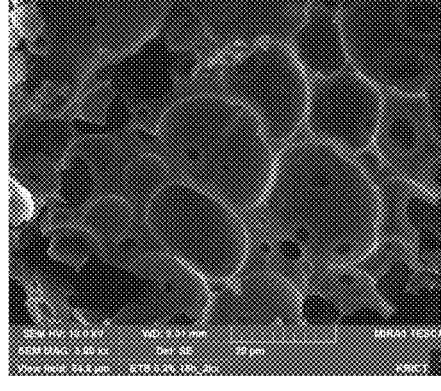 |

[Figure 3]
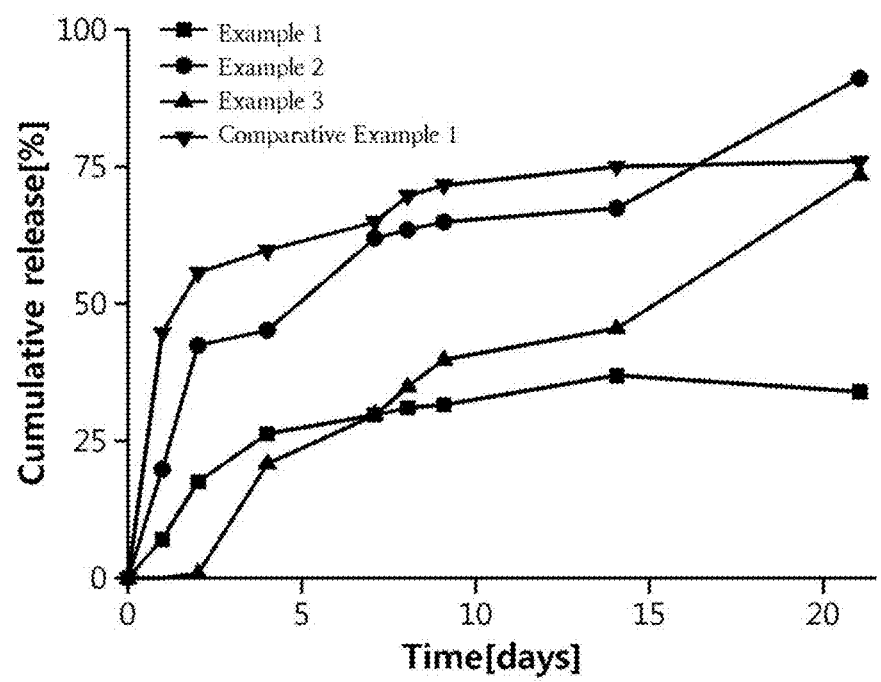

[Figure 4]
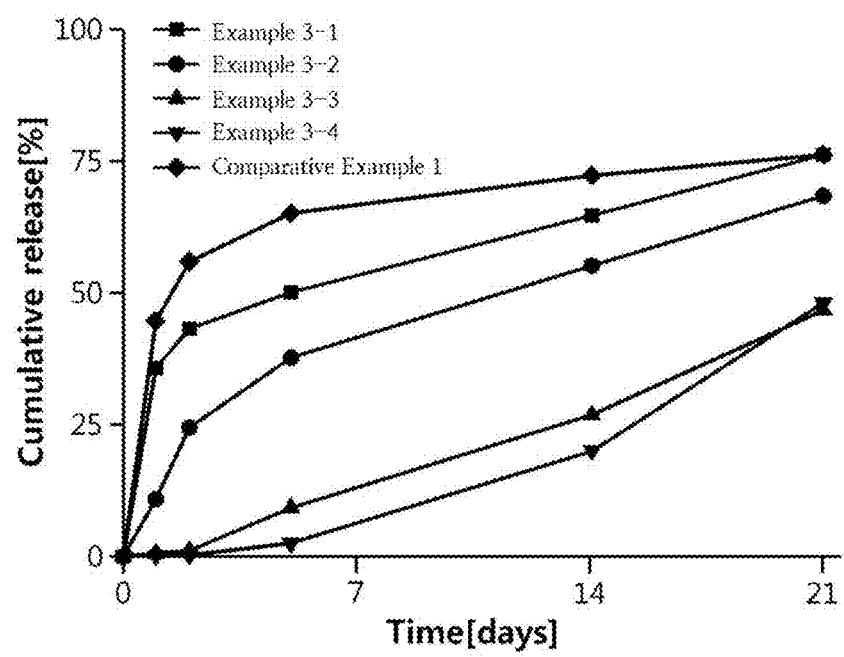

MICROSPHERICAL SUSTAINED-RELEASE INJECTION CONTAINING ESCITALOPRAM AND METHOD FOR PREPARING SAME

TECHNICAL FIELD

The present invention relates to an escitalopram sustained release formulation comprising biodegradable polymer microspheres and a manufacturing method thereof. More specifically, the sustained-release formulation is a drug carrier in which a predetermined amount of escitalopram is loaded into the biodegradable polymer microspheres. The formulation can maximize the loading amount and the encapsulation efficiency, suppress the initial over-release, and induce a sustained release of escitalopram for a certain period of time. The present invention also relates to a method for preparing the sustained-release formulation.

BACKGROUND ART

Patients having depression usually lack a neurotransmitter called serotonin in the brain. Escitalopram, antidepressant, acts to prevent serotonin from being reabsorbed in brain cells, thereby increasing serotonin in the brain. Escitalopram is the most representative 'selective serotonin reuptake inhibitor (SSRI)'.

Sustained release injection formulations, on the other hand, are injection formulations formulated to allow sustained and uniform release of the drug in the body after subcutaneous or intramuscular injection while maintaining biological activity. Conventional methods for preparing such sustained-release injection preparations are coacervation, melt injection, spray drying, solvent evaporation, and the like. Among these methods, solvent evaporation method is most commonly used, and solvent evaporation includes emulsion evaporation (W/O/W emulsion) and single emulsion evaporation (O/W emulsion). However, the microspheres made by a multiple emulsion method has a disadvantage of high initial release rate. In addition, the multi-emulsion method includes a step wherein a drug is dissolved in an organic solvent or water, which may problems such as changes in the properties of the drug, loss of drug efficacy, low encapsulation efficiency, and the like.

Various attempts have been made to increase the encapsulation rate of these sustained-release injections or to produce microspheres that are easy to manufacture and relatively low in initial over-release, but are not yet satisfactory. In 'active self-healing encapsulation of vaccine antigens in PLGA microspheres', Journal of Controlled Release 165 (2013) 62-74, microspheres were prepared by double emulsion evaporation, and the active vaccine antigen was loaded through the micropores of the microspheres. Next, the method heats the microspheres above the glass transition temperature (Tg) of the biodegradable polymer for blocking micropores, thereby inhibiting initial release. However, this manufacturing method has a serious disadvantage that the drug can be denatured by heat. In addition, the drug encapsulation efficiency was significantly increased by adding protein trapping agent (~97%), but the overall encapsulation amount of the active agent was significantly low (1.4~1.8%). This method has the disadvantage that the bioactive substance can be denatured by heat. In addition, there is a disadvantage that is not applicable in encapsulating a high dose of a drug with a large dose. In addition, there is a disadvantage that it is difficult to apply to the actual production due to the complex manufacturing process.

DETAILED DESCRIPTION

Technical Problem

Accordingly, it is an object of the present invention to provide an injection of biodegradable polymer microspheres comprising escitalopram as an active ingredient, which is capable of maximizing the encapsulation amount and encapsulation efficiency of escitalopram, improving the breaking of microspheres at high loading conditions, and properly controlling the initial release inhibition and release delay of microspheres. It is another object of the present invention to provide a method for preparing such microspheres.

Technical Solution

In order to solve the problem, the present invention provides a sustained release injection of biodegradable polymer microspheres comprising escitalopram (therein), wherein the microspheres additionally comprise a pharmaceutically acceptable hydrophobic solidifying agent so as to uniformly distribute escitalopram in a microsphere, and a method for manufacturing the same.

In general, escitalopram is in a liquid state when a biodegradable polymer, such as PLGA, is used to produce sustained release microspheres. Liquid state escitalopram is prepared in the form of O/O/W in which the solidified polymer and escitalopram are separated. This type of formulation results in a very low loading of escitalopram, and if the loading increases, the microspheres are present in the sponge form. The sponge type is difficult to maintain the shape of the microsphere due to the weak strength of the microspheres or is present in a broken form.

The present invention uses a pharmaceutically acceptable hydrophobic material like a fatty acid, an aromatic acid, a cholesterol derivative, a phospholipid, and the like in a microsphere to solidify escitalopram, which is normally a liquid. This changes an O/O/W microsphere formed by the liquid escitalopram to an O/W type microsphere, thereby increasing loading efficiency, and being capable of initial release inhibition and sustained release. The method of the present invention improves the sponge structure of the microspheres to manufacture a solid-phase microsphere having a uniform inside.

In the present invention, after body administration of the microspheres, the biodegradable polymer absorbs electrolyte in the body over time, and is hydrated and expanded so that the internal escitalopram is slowly released.

For the method according to the present invention, at least one hydrophobic fatty acid, an aromatic acid, a cholesterol derivative, and a phospholipid, which have properties of hydrophobic lipids existing in solid state in a body, are included in the microspheres. For example, fatty acids among the hydrophobic solidifying agents include a saturated fatty acid having 18 or more carbon atoms and having a melting point of 70° C. or more like stearic acid, and beheneic acid or the like. The aromatic acid includes be benzoic acid, salicylic acid, hydroxy naphthoic acid, naphthenic acid, naphthoic acid, naphthalic acid, pamoic acid, or the like, which have a melting point of 150° C. or more. Cholesterol derivatives include lithocholic acid, cholic acid, deoxycholic acid, and the like. Dipalmitoyl phosphoric acid (DPPA), dipalmitoyl phosphatidyl glycerol (DPPG), dipalmitoyl phosphatidyl serine (DPPS), and the like may be used as the phospholipid.

More preferably, for purposes of the present invention, stearic acid having a melting point of at least 70° C. may be used as the fatty acid, hydroxy naphthoic acid having a melting point of at least 150° C. may be used as the aromatic acid, lithocholic acid may be used as the cholesterol derivative, and DPPA (dipalmitoyl phosphoric acid) may be used as the phospholipid. These efficiently achieve the solidification of the escitalopram, maintain uniform and firm retention of the escitalopram inside the microspheres, and obtain high loadings of microspheres.

Most preferably, a hydroxy naphthoic acid is used as a pharmaceutically acceptable hydrophobic solidifying agent that is additionally comprised in the microspheres according to the present invention. When the hydroxy naphthoic acid is used, it is easy to manufacture microspheres with adequate strength, as well as to prepare microspheres to have a desired dissolution pattern.

In the microspheres according to the present invention, preferably, one or more of polylactide (PLA), polyglycolide (PGA), poly(lactide-co-glycolide) (PLGA), poly(lactide-co-glycolide) glucose, and the like can be used as the biodegradable polymer.

The present invention also provides a method for preparing a sustained release formulation comprising biodegradable polymer microspheres using a solvent intra-extraction evaporation method in O/W solvent (Solid-in-oil-in-water). The method allows for the production of sustained release formulations that maximize the encapsulation amount and encapsulation efficiency of the escitalopram in the microspheres and induce sustained and uniform release of the drug.

In other words, the present invention provides a method for preparing a biodegradable polymer microsphere-containing sustained release injection, comprising the steps of: preparing a solution containing a biodegradable polymer, escitalopram, and a pharmaceutically acceptable hydrophobic solidifying agent; and adding the solution to an aqueous solution to form an O/W emulsion and the microsphere.

More specifically, the present invention provides a manufacturing method comprising the steps of: (a) mixing a solvent with a biodegradable polymer, escitalopram, and a solidifying agent, and dissolving the same; (b) slowly mixing and stirring the solution with an aqueous solution (preferably a polyvinyl alcohol aqueous solution) to prepare an O/W emulsion; and (c) hardening in which microspheres are generated by diffusing and evaporating the co-solvent into the aqueous medium in the O/W emulsion. In addition, the manufacturing method according to the present invention may further comprise a step (d) of drying, preferably freeze-drying, the microspheres generated in the step (c).

Illustratively, the process of the present invention can be prepared through the following steps.

(Step a) Dissolving the Biodegradable Polymer, Escitalopram, and Solidifying Agent by Strong Mixing The non-aqueous solvent is not particularly limited if it can dissolve the biodegradable polymer. According to an embodiment of the present invention, a non-aqueous solvent having a low boiling point, for example, a boiling point of 25° C. to 85° C., can be used as the non-aqueous solvent. When the boiling point of the non-aqueous solvent is included in the range above, it is advantageous in terms of its evaporation and drying after generation of the microspheres. Examples of the non-aqueous solvent include, but are not limited to, dichloromethane, chloroform, acetonitrile, dimethylsulfoxide, dimethylformamide, ethyl acetate, and the like.

The biodegradable polymer is a conventional polymer used in preparing microspheres that can be used as a drug carrier, and is self-degradable in vivo and has biocompatibility. According to the present invention, one or more biodegradable polymers such as polylactide (PLA), polyglycolide (PGA), poly (lactide-co-glycolide) (PLGA), and poly (lactide-co-glycolide) glucose can be used.

In one specific embodiment of the present invention, the biodegradable polymer having a weight average molecular weight of 60,000 atomic mass units or less may be used. For example, poly (lactide-co-glycolide) (50:50) having a molecular weight of about 13,000 atomic mass units, poly (lactide-co-glycolide) (50:50) having a molecular weight of about 33,000 atomic mass units, poly (lactide-co-glycolide) (50:50) having a molecular weight of about 52,000 atomic mass units, poly (lactide-co-glycolide) (75:25) having a molecular weight of about 20,000 atomic mass units, and poly(lactide) (100:0) having a molecular weight of about 16,000 atomic mass units can be used. Such biodegradable polymers include, for example, the product sold under the trademark RESOMER® RG502H, RG503H, RG504H, RG752H, R202H of Berringers, Inc., and the like.

In one specific embodiment of the present invention, the biodegradable polymer having an intrinsic viscosity of 0.16 to 0.6 dL/g may be used. In the present invention, if the viscosity of the biodegradable polymer is less than 0.1 dL/g, the microspheres encapsulating the drug powder are not properly formed or the drug encapsulation rate is significantly reduced. If the intrinsic viscosity is greater than 0.6 dL/g, the size of the microspheres may be excessively large, and the amount of drug release may be less than the desired level of efficacy.

According to one specific embodiment of the present invention, the biodegradable polymer is dissolved in a concentration of 10 mg to 150 mg per ml of the first mixture, preferably 25 to 125 mg per ml, more preferably 50 to 125 mg per ml of the first mixture. When the concentration of the biodegradable polymer is small, the viscosity of the polymer solution is lowered so that the size of the microspheres becomes smaller when the biodegradable polymer is dispersed with the homogenizer. It appears that the ratio of the polymer in the microdroplet before the formation of the microsphere is small, thereby exhibiting a loose structure when the particle is formed, thereby lowering the encapsulation amount and the encapsulation efficiency of the drug. On the other hand, when the concentration exceeds 150 mg/ml, the size of the microsphere tends to increase as the viscosity of the polymer solution increases.

As the solidifying agent, the above-mentioned materials can be used.

(Step b) Adding the Solution to an Aqueous Solution and Slowly Mixing and Stirring to Prepare an O/W Emulsion.

The aqueous medium of the present invention may comprise an emulsifier. The amount of the emulsifier is preferably in the range of 0.1 g to 10 g, or 3 g to 7 g per 1 liter of the aqueous solvent, i.e., 0.1 (w/v) % to 10 (w/v) % or 3 (w/v) % to 7 (w/v) %. The emulsifier may include, but is not limited to, polysorbate, polyethylene glycol, polyvinyl alcohol, poloxamer, span 80, and the like. Preferably, the emulsifier in the present invention is polyvinyl alcohol.

In a specific embodiment of the present invention, in step b), the emulsion is prepared by mixing the suspension and the aqueous medium at a ratio of 1:5 to 1:50 based on the volume ratio. The mixing ratio is preferably 1:10 to 1:20.

When the volume ratio of the suspension to the aqueous medium is less than 1:5, the O/W emulsion is homogenized with a homogenizer, and the gap between microdroplets in the O/W emulsion becomes more likely to collide with each other so that fine droplets are agglomerated prior to diffusion and evaporation of the co-solvent and the non-aqueous solvent, thereby making it difficult to form microspheres with uniform size. In addition, when the ratio exceeds 1:50, the amount of emulsifier added increases and is disadvantageous in terms of cost.

(Step c) Hardening Step in which Microspheres are Generated while the Co-Solvent is Diffused and Evaporated into the Aqueous Medium in the O/W Emulsion.

In step b), primary polymer hardening is induced by diffusion and evaporation of the co-solvent into the aqueous medium, and thus the drug are incorporated in the microspheres. That is, as the co-solvent in the dispersed microdroplets in the O/W emulsion is rapidly diffused and extracted onto the aqueous solvent, the biodegradable polymer is rapidly solidified to form microspheres. According to one specific embodiment of the present invention, it is preferred that the microdroplets are strongly agitated with a magnetic stirrer so as not to agglomerate together in this process. The formation time of the microspheres may be in the range of 1 to 10 minutes. When the formation time of the microsphere is less than 1 minute, the biodegradable polymer of the microsphere is less hardened, thereby causing an agglomeration phenomenon between the microspheres. On the other hand, when more than 10 minutes, the encapsulation efficiency of the drug can be lowered.

After the microspheres are produced, the aqueous medium and solvent are removed from the O/W emulsion and microspheres are obtained.

(Step d) (Freeze-) Drying the Microspheres Produced in Step c.

Through the (freezing) drying process, the structure of the microsphere is robust and the drug is completely encapsulated in the biodegradable polymer. According to one specific embodiment of the present invention, the drying may further comprise a freeze drying step to completely remove the solvent remaining in the microspheres. The freezing step may be performed at a temperature of −30° C. to −40° C., and the drying time may be 12 to 24 hours. According to one specific embodiment of the present invention, the freeze drying step may be carried out under vacuum conditions. If the drying time is performed less than 12 hours, the residual solvent may not be completely removed, while if the drying time exceeds 24 hours, productivity may be lowered.

As described above, a biodegradable polymer microsphere, which is a sustained release formulation, can be manufactured by using the solvent intra-extraction evaporation in an O/W solvent (solid-in-oil-in-water) according to the present invention. The microspheres obtained according to the method have high drug encapsulation amount and encapsulation efficiency and excellent sustained release effects.

In the present invention, the microspheres may comprise 30 to 95 wt %, preferably 45 to 75 wt %, of biodegradable polymer relative to 100 wt % of microspheres. If the biodegradable polymer is contained in less than 40% by weight, the surface and the inside of the microspheres have a porous property, thereby causing the drug to be initially over-released or exhibit a short release time. On the other hand, if greater than 95% by weight, the amount of microspheres administered to a patient or animal may be too large to make the administration difficult, or the administration itself may be impossible.

Advantageous Effects

The present invention provides a polymer microsphere sustained release formulation capable of exhibiting sustained release behavior for a long period of time and having high encapsulation amount and efficiency by using a minimum process and energy of an extraction evaporation method in an O/W solvent in manufacturing biodegradable polymer microspheres comprising escitalopram, and a manufacturing method thereof. In particular, by including a solidifying agent capable of solidifying escitalopram in a microsphere, the encapsulation rate and the loading rate of the microspheres are increased and the internal structure of the microspheres is uniform, thereby efficiently controlling drug release.

DESCRIPTION OF DRAWINGS

The following drawings, which are to be incorporated in this specification, illustrate preferred embodiments of the invention and, together with the description of the invention, serve to further understanding the principles of the invention, and the invention is not to be construed as limited to the details set forth in such figures.

FIG. 1 is an electron micrograph of microspheres prepared in Example 1, Example 2, and Example 3. The left photograph is the entire picture of the microspheres and the right photograph is a photograph of the inside of the crushed surface of the microspheres. The microspheres prepared in Examples 1-3 show the inside filled morphology and the particles were not broken or deformed after drying.

FIG. 2 is a photograph of Comparative Example 1 in which the solidifying agent is not added in microspheres. Comparative Example 1 shows an emulsion in the form of an O/O/W emulsion, and the higher the content of the drug, the greater the number of small cells in which the liquid drug was present, resulting in a significant drop in the strength of the microspheres. As a result, after lyophilization, the broken form increased.

FIG. 3 is a graph showing in vitro drug release pattern measured according to Experimental Example 3 of microspheres prepared in Example 1, Example 2, Example 3 (3-3) and Comparative Example 1 according to the present invention. When the phospholipid (DPPA) is contained in comparison with Comparative Example 1, the initial release is shown, but the release delay effect is high as the time passes, and when the fatty acid (stearic acid) is added, the initial release and the release delay effect appear to be weak. In the case of Example 3, in which the aromatic acid was added, the initial release inhibition and the release delay effect were good.

FIG. 4 is a graph showing the results of comparison with Comparative Example 1 in Examples 3-1, 3-2, 3-3, and 3-4 according to the method of Example 3 of aromatic acid with good initial release inhibition and release delay effects. It can be seen that as the content of the aromatic acid increases, the initial release inhibition and the release delay effect are improved. This is because the O/O/W type non-uniform microsphere internal structure is changed into an O/W type uniform internal structure by the addition of a hydrophobic solidifying agent, thereby increasing the initial release inhibition and the release delay effect and preventing the microsphere from being broken even if the loading amount of escitalopram is increased.

MODE FOR INVENTION

Hereinafter, embodiments of the present invention will be described in detail in order to help an understanding of the present invention. This invention may, however, be embodied in many different forms and should not be construed as limited to the embodiments set forth herein.

Rather, these embodiments are provided so that this disclosure will be thorough and complete.

Example 1 Preparation of O/W Type Microspheres Using Biodegradable Polymer PLGA, Escitalopram, and DPPA 1.5 g of biodegradable polymer PLGA (Evonik, Product Name: RESOMSER® RG504H), 1 g of escitalopram, and 0.5 g of dipalmitoyl phosphoric acid (DPPA) were added to 20 ml of dichloromethane and stirred vigorously for 1 hour to dissolve them. The uniformly dissolved solution was placed in a 200 ml aqueous solution of 5 (w/v) % polyvinyl alcohol (SIGMA ALDRICH®, 87-90% hydrogenated MW: 30,000-70,000) and dispersed at 1,000-2,000 rpm using a homogenizer (IKA™, Ultra-Turrax™ T8) over 2 minutes to obtain an O/W emulsion. Thereafter, the emulsion was vigorously stirred at room temperature and atmospheric pressure to a magnetic stirrer (900 rpm) for 5 hours to form microspheres, and microspheres were collected using a Whatman paper and washed 2-3 times with distilled water. The washed microspheres were first dried at room temperature and atmospheric pressure for 3 hours, and then freeze-dried at −35° C. for 12 hours to completely remove the solvent in the microspheres.

Example 2 Preparation of O/W Type Microspheres Using Biodegradable Polymer PLGA, Escitalopram and Stearic Acid 1.5 g of biodegradable polymer PLGA (Evonik®, product name: RESOMER® RG504H®), 1 g of escitalopram and 0.3 g of stearic acid were added to 20 mL of dichloromethane and stirred vigorously for 1 hour to dissolve. Thereafter, the microspheres were prepared in the same manner as in Example 1.

Example 3 Preparation of O/W Type Microspheres Using Biodegradable Polymer PLGA, Escitalopram and 1-Hydroxy-2-naphthoic Acid 1.5 g of biodegradable polymer PLGA, 1 g of escitalopram, and 0.5 g of 1-hydroxy-2-naphthoic acid were added to 20 ml of dichloromethane and stirred vigorously for 1 hour to dissolve. Thereafter, the microspheres were prepared in the same manner as in Example 1.

Examples 3-1 to 3-4 were prepared in the same manner with varying amounts of 1-hydroxy-2-naphthoic acid. A representative example of Example 3 is Example 3-3.

TABLE 1

| | Example 3-1 | Example 3-2 | Example 3-3 | Example 3-4 |
|---|---|---|---|---|
| escitalopram | 1 g | 1 g | 1 g | 1 g |
| Hydroxy naphthoic Acid | 0.13 g | 0.3 g | 0.5 g | 0.63 g |
| PLGA(RG504H) | 1.5 g | 1.5 g | 1.5 g | 1.5 g |

Comparative Example 1: Preparation of O/O/W Type Microspheres Using Biodegradable Polymer PLGA and Escitalopram 1.5 g of biodegradable polymer PLGA (Evonik, Product Name: RESOMER® RG504H), and 1 g of escitalopram were added to 20 mL of dichloromethane and stirred vigorously for 1 hour to dissolve. Thereafter, the microspheres were prepared in the same manner as in Example 1.

Experimental Example 1: Morphology Measurement of Microspheres

The morphology of the microspheres obtained in Examples 1 to 3 and Comparative Example 1 was confirmed using an electron microscope. A sample for observing the crushing surface was prepared by adding 100 mg of microspheres and 5 ml of liquid nitrogen to the pestle and crushing the particles. About 5 mg of the prepared microspheres were coated with a platinum coating for 4 minutes using a coater (Quorum™ Q150 TES, 10 mA), and the morphology and surface of the microspheres were observed through a scanning electron microscope (sold under the trademark TESCAN® Mira™ 3, LMU FEG-SEM).

The results are shown in FIGS. 1 and 2. According to the results, microspheres having a size of about 50-160 μm were identified in each of the Examples and Comparative Examples, and Comparative Example 1 showed the formation of sponge-shaped pores inside the microspheres by phase separation between the liquid escitalopram and the PLGA polymer, thereby significantly lowering the strength of the microspheres. Examples 1-3, on the other hand, were in the form of a filled solid and had little broken morphology. The stearic acid of Example 1 showed a soft and slightly distorted spherical shape due to the influence of lipid, and the phospholipid (DPPA; dipalmitoyl phosphoric acid) of Example 2 showed a shape in which the inner crushing surface was filled with a solid without pores or cracks, but the surface was somewhat rough. Example 3 was an aromatic hydroxy-naphthoic acid-containing particulate, the particle shape was spherical and the surface was homogeneous. The inner crushing surface was observed to have a small number of pores, but the number was not large.

Experimental Example 2: Determination of the Encapsulation Amount and Rate of Escitalopram of Microspheres About 30 mg of microspheres prepared in Examples 1-3 and Comparative Example 1 were completely dissolved in 3 ml of chloroform (SIGMA ALDRICH®), and then diluted to 400-fold to be used as a test solution. The absorbance was measured using an HPLC photometer to determine the content of escitalopram encapsulated in the microspheres. The encapsulation rate was calculated as the encapsulated amount relative to the added amount of the drug.

HPLC analysis conditions were as follows:

The mobile phase was prepared at a ratio of Acetonitrile 4:Methanol 5:Buffer 11; the detector was UV 240 nm; the separation column was 4.6-mm×25-cm; 5-um packing L1; the flow rate was 1.5 ml/min; the injection size was 20 uL; the analysis time was 15 min; and the assay range was measured in a concentration range of 1000 ug/ml to 7.8125 ug/ml.

The results are shown in Table 2.

TABLE 2

|  | Content rate of drug (%) (Encapsulated amount of drug/weight of microsphere) × 100 (%) | Encapsulation Efficiency (%) (Encapsulated amount of drug/Added amount of drug) × 100% |
|---|---|---|
| Example 1 | 35.7 ± 0.6 | 75.5 ± 0.2 |
| Example 2 | 34.4 ± 0.2 | 78.3 ± 0.4 |
| Example 3 | 34.6 ± 0.4 | 84.2 ± 0.6 |
| Comparative Example 1 | 12.5 ± 0.2 | 46 ± 0.5 |

The encapsulation efficiency of escitalopram in Examples 1-3 has been as high as 75-80%. However, Comparative Example 1 had a relatively low encapsulation rate because the drug was lost in liquid phase. The content of the drug of Comparative Example 1 was also low, and it seems that it is because the microspheres of the sponge structure were broken or the non-ideal release happened.

Experimental Example 3: Measurement of In Vitro Drug Release Behavior of Microspheres In order to measure the release behavior of the drug, the microspheres prepared in Examples 1-3 and Comparative Example 1 were weighed so that the amount of drug in the microspheres was 4.0 mg and stored in 100 ml of PBS (Phosphate Buffered Saline, pH 7.4) at 37° C. isotherm, and the amount of release was measured using a HPLC by diluting 1 ml of the PBS to 40-fold every hour. The concentration of the released drug was calculated by converting the absorbance value, and the amount of drug released for each time relative to the total drug (4 mg) of each sample was calculated as a cumulative percentage. The escitalopram stock solution was used as a control for this experiment. The results of these measurements are shown in FIGS. 3 and 4.

FIG. 3 is a graph showing in vitro drug release behavior measured according to Experimental Example 3 of microspheres prepared in Example 1, Example 2, Example 3 (3-3) and Comparative Example 1 according to the present invention. As compared to Comparative Example 1, when the phospholipid (DPPA) was contained, the initial release was shown, but the release delay effect was increased over time. When the fatty acid (stearic acid) was added, the initial release and the release delay effect appeared to be weak. In the case of Example 3, which is the case where aromatic acid was added, the initial release inhibition and the release delay effect were good.

FIG. 4 is a graph showing the results of comparison with Comparative Example 1 in Examples 3-1, 3-2, 3-3, and 3-4 according to the method of Example 3 of aromatic acid with good initial release inhibition and release delay effects. It can be seen that as the content of the aromatic acid increases, the initial release inhibition and the release delay effect are improved. This is because the O/O/W type non-uniform microsphere internal structure is changed into an O/W type uniform internal structure by the addition of a hydrophobic solidifying agent, thereby increasing the initial release inhibition and the release delay effect and preventing the microsphere from being broken even if the loading amount of the escitalopram is increased.

The invention claimed is:

1. A sustained release injectable composition, comprising biodegradable polymer microspheres comprising escitalopram,
wherein the microspheres further comprise a pharmaceutically acceptable hydrophobic solidifying agent to uniformly distribute the escitalopram in the microspheres,
wherein the biodegradable polymer is selected from at least one of the group consisting of polylactide, polyglycolide, poly (lactide-co-glycolide), and poly (lactide-co-glycolide) glucose, and
wherein the pharmaceutically acceptable hydrophobic solidifying agent is selected from the group consisting of dipalmitoyl phosphoric acid, stearic acid, lithocholic acid, hydroxy naphthoic acid, and a mixture thereof.

2. The sustained release injectable composition of claim 1, wherein the pharmaceutically acceptable hydrophobic solidifying agent is a hydroxy naphthoic acid.

* * * * *